US00PP13479P2

(12) United States Plant Patent
Bradford

(10) Patent No.: US PP13,479 P2
(45) Date of Patent: Jan. 14, 2003

(54) NECTARINE TREE NAMED 'LATE PEARL'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/014,016

(22) Filed: Dec. 13, 2001

(51) Int. Cl.[7] ..... A01H 5/00
(52) U.S. Cl. ..... Plt./188; Plt./189
(58) Field of Search ..... Plt./188, 189

(56) References Cited

U.S. PATENT DOCUMENTS

PP5,664 P 2/1986 Bradford ..... Plt./190
PP9,358 P 11/1995 Bradford ..... Plt./188

*Primary Examiner*—Bruce R. Campell
*Assistant Examiner*—W C Haas

(57) ABSTRACT

The present invention relates to a nectarine tree, *Prunus persica*, and more particularly to a new and distinct variety broadly characterized by a medium size, vigorous, hardy, self-fertile, and productive tree that produces fruit that is uniformly medium in size, very good in flavor, globose in shape, clingstone in type, firm in texture, white in flesh color, and partially red in skin color. The fruit matures under the ecological conditions described approximately the first week in September, with first picking on Sep. 5, 2001. The variety was developed as a first generation cross using Fire Pearl (U.S. Plant Pat. No. 9,358) white flesh nectarine as the selected seed parent and September Red (U.S. Plant Pat. No. 5,664) yellow flesh nectarine as the selected pollen parent.

1 Drawing Sheet

BOTANICAL CLASSIFICATION

*Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'LATE PEARL'. The present variety was hybridized by me in 1996, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'Fire Pearl' (U.S. Plant Pat. No. 9,358) white flesh nectarine as the selected seed parent and 'September Red' (U.S. Plant Pat. No. 5,664) yellow flesh nectarine as the selected pollen parent. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its selected seed parent, 'Fire Pearl' (U.S. Plant Pat. No. 9,358) nectarine, by producing nectarines that are globose in shape, firm in texture, white in flesh color, and subacid and sweet in flavor, but is distinguished therefrom and an improvement thereon by producing fruit that matures about thirty-five days later.

The present variety is similar to its selected pollen parent, 'September Red' (U.S. Plant Pat. No. 5,664) nectarine, by producing nectarines that are medium in size, that are partially red in skin color and that mature in early September, but is distinguished therefrom and an improvement thereon by having globose instead of reniform glands and by producing fruit that is white in flesh color instead of yellow.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin County), Calif., and was developed at the state of full ripe on Sep. 12, 2001, on the original tree during its fifth growing season. All major color code designations are by reference to the Inter-Society Color Council, National Bureau of Standards. Common color names are also used.

Tree

Size: Medium, reaching a height of 8' [2.44 m.] after five growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Vase formed.
Hardiness: Hardy with respect to central California winters.
Heat tolerance: Observed to perform adequately in typical central California climatic conditions, which typically include prolonged periods of heat.
Drought tolerance: Variety is developed for commercial orchards and requires regular irrigation.

Production: Productive, thinning usually necessary.
Fertility: Self-fertile.
Bearing: Usual bearer with a light crop observed once.
Trunk:
*Size.*—Medium, reaching a maximum diameter of 3¾" [95 mm.] after the fifth growing season.
*Texture.*—Shaggy.
*Bark color.*—Grayish brown [61. gy.Br].
*Lenticels.*—Numerous. Color: Dark orange yellow [72. d.OY]. Average Size: ⅜" [9.5 mm.].
Branches:
*Size.*—Diameter of scaffold is 1⅞" [48 mm.] measured 12" above the crotch, typical of *Prunus persica*, and dependent upon cultural practices and climatic conditions.
*Texture.*—Smooth on 1st year wood, increasing roughness with age.
*Color.*—1st Year Wood Topside: Grayish red [19. gy.R]. 1st Year Wood Underside: Brilliant yellow green [116. brill.YG]. Older Wood: Deep yellowish brown [75. deep yBr].
*Lenticels.*—Numerous. Color: Strong orange yellow [68. s.OY]. Average Size: 1/16" [1.6 mm.].
Leaves:
*Size.*—Medium. Average Length: 5½" [140 mm.]. Average width: 1⅝" [41 mm.].
*Arrangement.*—Alternate.
*Thickness.*—Medium.
*Form.*—Elliptical.
*Apex.*—Acuminate.
*Base.*—Acute with an average angle of eighty degrees.
*Surfaces.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: ⅜" [9.5 mm.]. Average Thickness: 1/16" [1.6 mm.]. Color: Light yellow green [119. l.YG].
*Stipules.*—Number: 2 per leaf, up to 6 per growing tip. Average Length: ⅜" [9.5 mm.]. Color: Brilliant yellow green [116. brill.YG] when growing.
*Glands.*—Number: Mostly 2, occasionally more. Position: Alternately positioned on the petiole and base of blade. Size: Small. Form: Globose. Color: Brilliant yellow green [116. brill.YG] on newer leaves acquiring Dark reddish brown [44. d.rBr] centers on with age.
*Leaf buds.*—Pointed.
Flower buds:
*Hardiness.*—Hardy, with respect to central California winters.
*Diameter.*—Typically ⅜" [9.5 mm.] 1 week before bloom.
*Length.*—Typically ¾" [19.1 mm.] 1 week before bloom.
*Form.*—Not appressed.
*Surface.*—Pubescent.
*Color.*—Strong purplish pink [247. s.pPk].
Flowers: Perfect, complete, perigynous, usually a single pistil, typically thirty or more stamens, five sepals and petal locations alternately positioned.
*Type.*—Large, showy.
*Average flower diameter.*—1¾" [44.5 mm.].
*Number of petals.*—Usually five, very few doubles.
*Petal shape.*—Circular.
*Petal margin.*—Slightly wavy.
*Average petal diameter.*—11/16" [17.5 mm.].
*Average petal length.*—11/16" [17.5 mm.].
*Petal apex.*—Rounded.
*Petal base.*—Rounded, wavy.
*Petal color.*—Pale purplish pink [252. p.pPk] toward the apex becoming Deep purplish pink [248. deep pPk] near the base.
*Anther color.*—Dark red [16. d.R] when first open.
*Stigma color.*—Light yellow [86. l.Y].
*Sepal color.*—Very deep purplish red [257. v.deep pR].
*Sepal length.*—5/32" [4 mm.].
*Sepal width.*—3/16" [5 mm.].
*Average pistil length.*—¾" [19.1 mm.].
*Average stamen length.*—⅝" [15.9 mm.].
*Fragrance.*—Moderate when nectar is present.
*Blooming period.*—Medium compared with other varieties.
*Onset of bloom.*—One percent on Feb. 24, 2001.
*Date of full bloom.*—Mar. 3, 2001.
*Duration of bloom.*—One to two weeks, dependent on ambient temperature.
*Number per cluster.*—Mostly 1, occasionally 2, rarely more than 2.

FRUIT

Maturity when described: Full ripe, Sep. 12, 2001.
Date of first picking: Sep. 5, 2001.
Date of last picking: Sep. 15, 2001.
Size: Uniform, medium.
*Average diameter axially.*—2 7/16" [62 mm.].
*Average diameter across suture plane.*—2 9/16" [65 mm.].
*Typical weight.*—6.0 ounces [170 grams].
Form: Uniform, symmetrical, globose with slight axial compression.
*Longitudinal section form.*—Roundish, compressed toward the poles.
*Transverse section through diameter.*—Roundish.
Suture: A shallow sharp groove near the base, a distinguishable line at mid-suture, and a shallow groove with a moderate depression beyond the pistil point toward the apex.
Ventral surface: Rounded, lipped toward the apex.
Lips: Equal toward the apex, but one side protruding more than the other along the mid-suture area.
Cavity: Flaring, elongated in the suture plane, suture showing on one side, Yellowish white [92. yWhite] stem markings typical.
*Depth.*—½" [12.7 mm.].
*Breadth.*—⅞" [22.2 mm.].
Base: Truncate.
Apex: Rounded.
Pistil point: Oblique, about 1/16" [1.6 mm.] in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—Slight in wet season.

*Color.*—Dark red [16. d.R] over a Yellowish white [92. yWhite] background with some Strong orange yellow [68. s.OY] freckling more pronounced toward the apex.

Flesh:

*Color.*—Yellowish white [92. yWhite] toward the skin with substantial Moderate red [15. m.R] streaking becoming Very dark red [17. v.d.R] near the stone.

*Surface of pit cavity.*—Very dark red [17. v.d.R] fibers breaking when twisted from the stone.

*Amygdalin.*—Scarce.

*Juice.*—Abundant, rich.

*Texture.*—Firm, crisp.

*Fibers.*—Abundant, fine.

*Ripens.*—Slightly earlier toward the apex.

*Flavor.*—Subacid and very sweet, averaging 16 brix.

*Aroma.*—Slight.

*Eating quality.*—Very good.

STONE

Type: Clingstone.
Form: Oval.
Hilum: Narrow, oblong.
Base: Straight.
Apex: Acute.
Sides: Equal.
Surface: Irregularly furrowed near the apex and pitted toward the base.
Ridges: Jagged toward the base.
Color: Dark reddish brown [44. d.rBr].
Average pit wall thickness: ¼" [6.4 mm.].
Average width: 1" [25.4 mm.].
Average length: 1 5/16" [33.3 mm.].
Average breadth: 11/16" [17.5 mm.].
Kernel:

*Form.*—Oval.

*Pellicle color.*—Grayish yellowish brown [80. gy.yBr].

*Skin color.*—Strong yellowish brown [74. s.yBr].

*Vein color.*—Grayish yellowish brown [80. gy.yBr].

*Taste.*—Very bitter.

*Viable.*—Yes.

*Average width.*—½" [12.7 mm.].

*Average length.*—¾" [19.1 mm.].

*Amygdalin.*—Abundant.

USE

Market: Fresh market and long distance shipping.
Keeping quality: Good. Fruit quality observed to remain in good condition in after 14 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new vareity of nectarine tree possesses the described charcteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree that is similar to its selected seed parent, 'Fire Pearl' (U.S. Plant Pat. No. 9,358) nectarine, by producing nectarines that are globose in shape, firm in texture, white in flesh color, and subacid in flavor; and that is similar to its selected pollen parent, 'September Red' (U.S. Plant Pat. No. 5,664) nectarine, by producing nectarines that are medium in size, partially red in skin color and mature in early September; but is distinguished therefrom and an improvement thereon by combining these desirable traits to produce the unique nectarine tree as illustrated and described.

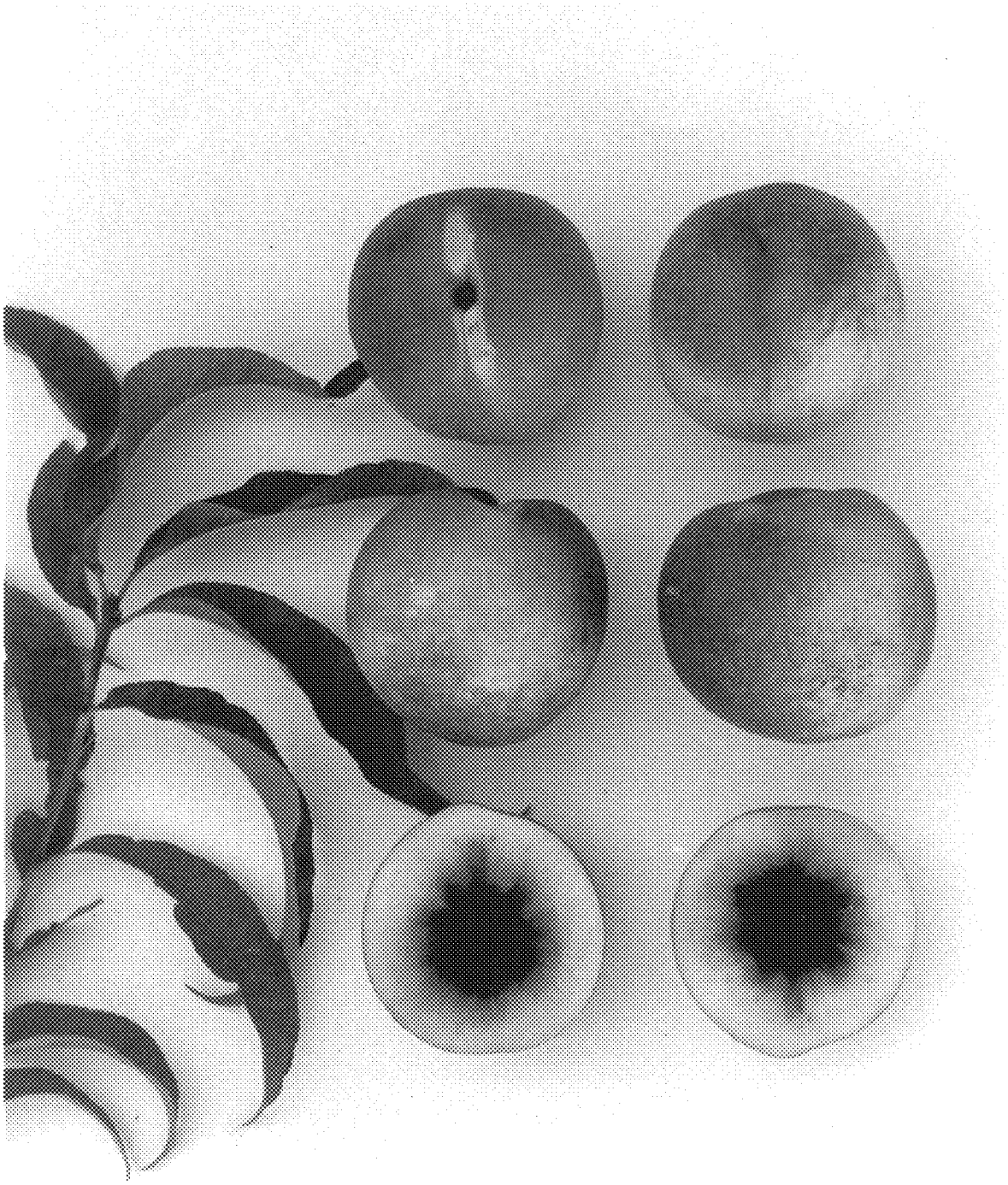

* * * * *